United States Patent [19]

Elsberry et al.

[11] Patent Number: 5,735,814
[45] Date of Patent: Apr. 7, 1998

[54] TECHNIQUES OF TREATING NEURODEGENERATIVE DISORDERS BY BRAIN INFUSION

[75] Inventors: Dennis D. Elsberry, New Hope; Mark T. Rise, Monticello, both of Minn.

[73] Assignee: Medtronic, Inc., Minneapolis, Minn.

[21] Appl. No.: 640,358

[22] Filed: Apr. 30, 1996

[51] Int. Cl.$^6$ ............................................. A61K 9/22
[52] U.S. Cl. ................................. 604/43; 604/49
[58] Field of Search ............................ 604/43, 49, 50, 604/51, 93, 891.1

[56] References Cited

U.S. PATENT DOCUMENTS

| | | | |
|---|---|---|---|
| 4,692,147 | 9/1987 | Duggan. | |
| 5,293,879 | 3/1994 | Vonk et al.. | |
| 5,403,278 | 4/1995 | Ernst et al. | 604/49 |
| 5,487,739 | 1/1996 | Aebischer et al. | 604/93 |

FOREIGN PATENT DOCUMENTS

WO9401166  1/1994  WIPO.

OTHER PUBLICATIONS

Duncan et al., "Thalamic VPM Nucleus In The Behaving Monkey, III. Effects of Reversible Inactivation by Lidocaine on Thermal and Mechanical Discrimination," *J. Neurophysiology*, vol. 70, No. 5, pp. 2086–2096 (1993).

Bobo et al., "Convection–enhanced delivery of macromolecules in the brain," *Proc. Natl. Acad. Sci. USA*, 91, pp. 2076–2080 (1994).

Crossman et al., "Experimental Hemiballismus In The Baboon Produced By Injection Of A Gamma–Aminobutyric Acid Antagonist Into The Basal Ganglia," *Neuroscience Letters*, 20 pp. 369–372 (1980).

Graham et al., "Injection of Excitatory Amino Acid Antagonists Into The Medial Pallidal Segment of a 1–Methyl–4–Phenyl–1,2,3,6–Tetrahydropyridine (MPTP) Treated Primate Reverses Motor Symptoms Of Parkinsonism", *Life Sciences*, 47, pp. 91–97 (1990).

van Horne et al., "Multichannel Semiconductor–based electrodes for in vivo electrochemical and electrophysical studies in rat CNS", *Neuroscience Letters*. 120, pp. 249–252 (1990).

Couratier et al., "Cell culture evidence for neuronal degeneration in amyotrophic lateral sclerosis being linked to glutamate AMPA/kainate receptors", *The Lancet*, vol. 341 (Jan. 30, 1993).

Shaw et al., "Studies on Cellular Free Radical Protection Mechanisms in the Anterior Horn from Patients with Amyotrophic Lateral Sclerosis", *Neurodegeneration*, vol. 4, pp. 391–396 (1995).

Yamauchi et al., "Corpus Callosum atrophy in amyotrophic lateral sclerosis", *J. Neurological Sciences*, 134, pp. 189–196 (1995).

Hollander et al., "High–dose Dextromethorphan in Amyotrophic Lateral Sclerosis: Phase I Safety and Pharmacokinetic Studies", *Ann. Neurol.* 36, pp. 920–924 (1994).

Nihei et al., "NPY Immunoreactive Neurons Are Involved In the Degeneration Of Amyotrophic Lateral Sclerosis", *Biomedical Research* 15, Suppl. 2, pp. 209–212 (1994).

Lanius et al., "A Role for Amplified Protein Kinase C Activity in the Pathogenesis of Amyotrophic Lateral Sclerosis", *J. Neurochemistry*, p. 927 (1995).

(List continued on next page.)

*Primary Examiner*—Michael Buiz
*Assistant Examiner*—Kevin Truong
*Attorney, Agent, or Firm*—Banner & Witcoff, Ltd.

[57] ABSTRACT

Techniques for infusing drugs into the brain to treat neurodegenerative disorders by an implantable pump and catheter. The drugs are capable of altering the level of excitation of neruons in the brain. A sensor is used to detect an attribute of the nervous system which reflects the hyperexcitation of the nerve cells projecting onto the degenerating nerve cells. A microprocessor algorithm analyzes the output from the sensor in order to regulate the amount of drug delivered to the brain.

25 Claims, 2 Drawing Sheets

OTHER PUBLICATIONS

Appel, "Excitotoxic neuronal cell death in amyotrophic lateral sclerosis", *TINS*, vol. 16, No. 1, pp. 3–5 (1993).

Rothman et al., "Excitotoxicity and the NMDA receptor", *TINS* vol. 10, No. 7, pp. 299–302 (1987).

Benabid et al., "Long-term suppression of tremor by chronic stimulation of the ventral intermediate thalamic nucleus", *The Lancet*, vol. 337, pp. 403–406 (1991).

Benabid et al., "Vim and STN Stimulation in Parkinson's Disease", *Movement Disorders*, vol. 9, Suppl. 1, Abstract M39 (1994).

Limousin et al., "Effect on Parkinsonian signs and symptoms of bilateral subthalamic nucleus stimulation", *The Lancet*, vol. 345, pp. 91–95 (1995).

Bensimon et al., "A Controlled Trial of Riluzole in Amyotrophic Lateral Sclerosis", The New England Journal of Medicine, vol. 330, No. 9, pp. 585–591 (1994).

TECHNIQUES OF TREATING NEURODEGENERATIVE DISORDERS BY BRAIN INFUSION

BACKGROUND OF THE INVENTION

1. Field of the Invention

This invention relates to brain infusion techniques, and more particularly relates to such techniques for treating neurodegenerative disorders.

2. Description of Related Art

Neuroscientists have recognized and continue to explore excitotoxicity, a phenomenon referring to excessive excitation of nerve cells leading to degeneration of the nervous system. This phenomena has been used to explain cell loss after stroke or some other hypoxic event. The research has focused on nerve cells that have glutamate neurotransmitter receptors especially susceptible to the sustained insult. Hyperexcitation of these nerve cells is fundamental to the mechanism (Rothman, S. M., Olney, J. W. (1987) *Trends Neurosci.* 10, 299–302). Researchers have also used excitotoxicity to explain the observed cell loss in the CA1 region of the Horn of Ammon in the dentate gyrus of hippocampus in patients and animal subjects that have suffered from seizure activity. Seizures can be viewed as a form of abnormal over excitation of the nerve cells in this region.

Typically, neuroscientists have focused on nerve cells that use the transmitter substance glutamate to communicate with target nerve cells; however, other excitatory amino acids (EAA) are included. When nerve cells are abnormally active, experiencing excessive action potentials, they are believed to release excessive amounts of glutamate or other EAA at their synaptic terminals. The presence of excessive amounts of glutamate leads to toxic effects on the secondary nerve cells targeted by the hyperactive ones. These toxic effects are believed to be mediated by an accumulation of calcium.

Benabid et al. (*The Lancet*, Vol 337:Feb 16, 1991, pp 403–406) has shown that stimulation of the Vim nucleus of the Thalamus will block tremor. In this instance, stimulation at frequencies around 100 to 185 pulses per second accomplishes the same physiological response as a lesion of this region. Thus, it appears that stimulation inhibits the output of these cells. Benabid's research team has extended this work to stimulation of the subthalamus ("Vim and STN Stimulation in Parkinson's disease", *Movement Disorders*, Vol.9, Supplement 1 (1994); "Effect on Parkinsonian signs and symptoms of bilateral subthalamic nucleus stimulation", *The Lancet*, Vol 345, Jan. 14, 1995.

Parkinson's disease is the result of degeneration of the substantia nigra pars compacta. The cells of subthalamus have been shown to use glutamate as the neurotransmitter effecting communication with their target cells of the basal ganglia. The state of hyperexcitation that exists in Parkinson's disease will cause an excessive release of glutamate. This, in theory, will lead to further degeneration via the mechanism described above.

Benabid has proposed a method of arresting degeneration of the substantia nigra by high frequency electrical pulsing of the subthalamic nucleus to block stimulation of the subthalamic nucleus, thereby inhibiting excessive release of glutamate at the terminal ends of the axons projecting from the subthalamic nucleus to the substantia nigra.

Amotrophic Lateral Sclerosis (ALS), sometimes referred to as Lou Gerhig's disease, is a progressive neurodegenerative disease affecting the voluntary motor system. The degeneration of the spinal cord and cortical motor neurons results in paralysis, respiratory depression and death. Glutamate neurons appear to be overactive in this disease state and are suspected of causing the neurodegeneration (S. H. Apel, "Excitotoxic neuronal cell death in amyotrophic lateral sclerosis", TINS, Vol. 16, No. 1, 1993).

Huntington's disease is a degnerative disorder characterized by choreathetosis which is at first slight. Usually, the choreathetosis is accompanied by hypotonus. The motor dysfunction, associated with excitatory transmitter neurotoxicity, may be accompanied by subtle forms of mental disorder that progress to a deterioration of cognitive function.

SUMMARY OF THE INVENTION

A preferred form of the invention can treat a neurodegenerative disorder, such as Parkinson's disease Huntington's or Amyotrophic Lateral Sclerosis (ALS), by means of an implantable pump and a catheter having a proximal end coupled to the pump and having a discharge portion for infusing therapeutic dosages of the one or more drugs capable of altering the level of excitation of neurons of the brain. The catheter is implanted in the brain so that the discharge portion lies adjacent to a predetermined infusion site in the basal ganglia or thalamus of the brain. Alternatively, the catheter may be implanted in a ventricle of the brain or subdurally so that the discharge portion lies within the cerebral spinal fluid (CSF). The pump is operated to discharge a predetermined dosage of the one or more drugs through the discharge portion of the catheter into the infusion site. By using the foregoing method, the neurodegeneration that occurs in diseases, such as Parkinson's disease, Huntington's disease and Amyotrophic Lateral Sclerosis, can be alleviated or prevented.

According to one embodiment of the invention, one or more drugs can decrease excitement of the subthalamus or increase inhibition of the subthalamus. According to another embodiment of the invention, the one or more drugs can increase excitement of the thalamus or decrease inhibition of the thalamus.

Another form of the invention uses a sensor in combination with the implantable pump and catheter to administer one or more drugs capable of altering the level of excitation of nerurons of the brain to treat a neurodegenerative disorder. In this form of the invention, the sensor generates a signal relating to an attribute of the nervous system which indicates the hyperexcitation of the degenerating neurons or the neurons related to the degenerating neurons. Control means responsive to the sensor signal regulate the therapeutic dosage. For example, the dosage can be increased in response to an increase in the hyperexcitation of the neurons and is decreased in response to a decrease in the hyperexcitation of the neurons.

By using the foregoing techniques, neurodegeneration can be controlled to a degree unattainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
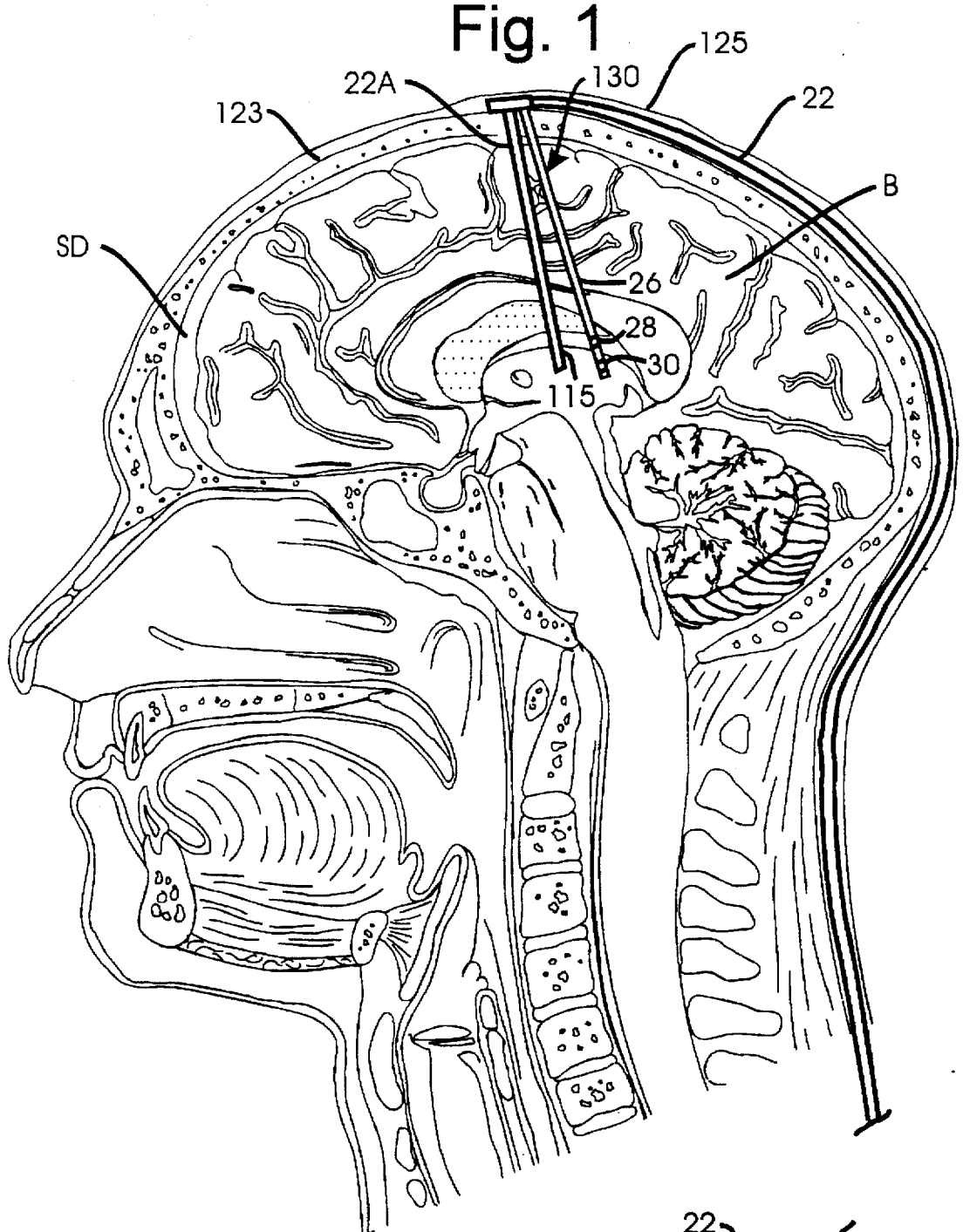
FIG. 1 is a diagrammatic; illustration of a portion of the nervous system of the human body in which a preferred form of hyperexcitation sensor, pump and catheter have been implanted.
Figure 1:
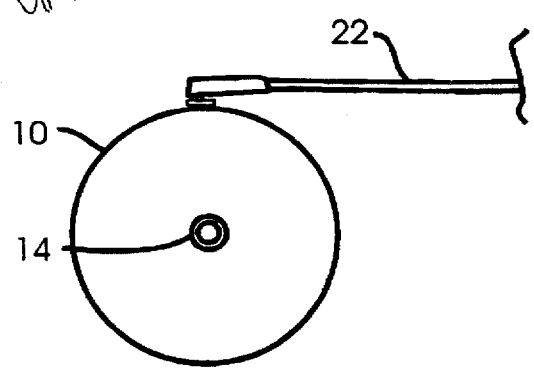

Referring to FIG. 1, a system or device 10 made in accordance with the preferred embodiment may be implanted below the skin of a patient. The device has a port 14 into which a hypodermic needle can be inserted through the skin to inject a quantity of a liquid agent, such as a medication or drug. The liquid agent is delivered from device 10 through a catheter port 20 into a catheter 22. Catheter 22 is positioned to deliver the agent to specific infusion sites in a brain (B). Device 10 may take the form of the like-numbered device shown in U.S. Pat. No. 4,692, 147 (Duggan), assigned to Medtronic, Inc., Minneapolis, Minn., which is incorporated by reference.

The distal end of catheter 22 terminates in a cylindrical hollow tube 22A having a distal end 115 implanted into a portion of the basal ganglia of the brain by conventional stereotactic surgical techniques. Additional details about end 115 may be obtained from pending U.S. application Ser. No. 08/430,960 entitled "Intraparenchymal Infusion Catheter System," filed Apr. 28, 1995 in the name of Dennis Elsberry et al. and assigned to the same assignee as the present application. Tube 22A is surgically implanted through a hole in the skull 123 and catheter 22 is implanted between the skull and the scalp 125 as shown in FIG. 1. Catheter 22 is joined to implanted device 10 in the manner shown. Device 10 is implanted in a human body in a subcutaneous pocket located in the chest below the clavicle. Alternatively, device 10 may be implanted in the abdomen.

In a second embodiment, distal end 115 of cylindrical hollow tube 22A may be implanted in a ventricle. Alternatively, the distal tip may be located in subdural area SD beneath the dura under the skull 123 but outside the brain B.

Catheter 22 may be divided into twin tubes 22A and 22B (not shown) that are implanted into the brain bilaterally. Alternatively, tube 22B (not shown) implanted on the other side of the brain may be supplied with drugs from a separate catheter and pump.

A sensor 130 is implanted into a portion of a patient's central nervous system. As shown in FIG. 1, sensor 130 comprises a sensing lead 26 having two sensing electrodes 28 and 30 located in the subthalamic region, substantia nigra or other brain region whose electrical activity indicates the activity of the degenerating neurons, i.e., the neurons exhibiting hyperexcitation. Alternatively, electrodes 28 and 30 could be carried by tube 22A. Electrodes 28 and 30 are connected to an analog to digital converter 140 (FIG. 2) by conductors 134 and 135 which are located within catheter 22. The potentials sensed by electrodes 28 and 30 indicate the electrical activity in the subthalamic nucleus and consequently the substantia nigra. Electrodes 28 and 30 transmit a signal related to the excitation of the portion of the brain exhibiting hyperexcitation. More specifically, electrodes 28 and 30 sense an attribute of the nervous system which indicates the hyperexcitation of the nerve cells projecting onto the degenerating nerve cells or the hyperexcitation of the degenerating nerve cells. Sensor 130 may take the form of a device capable of detecting nerve cell electrical activity that is related to the hyperexcitation. Such a sensor may be located deep in the brain. For such detecting, sensor 130 may take the form of an electrode inserted into one of the nuclei of the basal ganglia, the thalamus, the internal capsule or the cortex of the brain. Alternatively, such a sensor may be located outside the dura in the bone of the cranium. Signals that are received by the sensor may by amplified before transmission to circuitry contained within device 10.

Alternatively, sensor 130 may electronically transduce the concentration of a transmitter substance infused into the brain or released endogenously. A paper describing such a sensor is entitled "Multichannel Semiconductor-based Electrodes for In Vivo Electrochemical and Electrophysiological Studies in Rat CNS", by van Horne et al., 120 *Neuroscience Letters* 249–252 (Elsevier Scientific Publishers Ireland Ltd. 1990).

Figure 2:
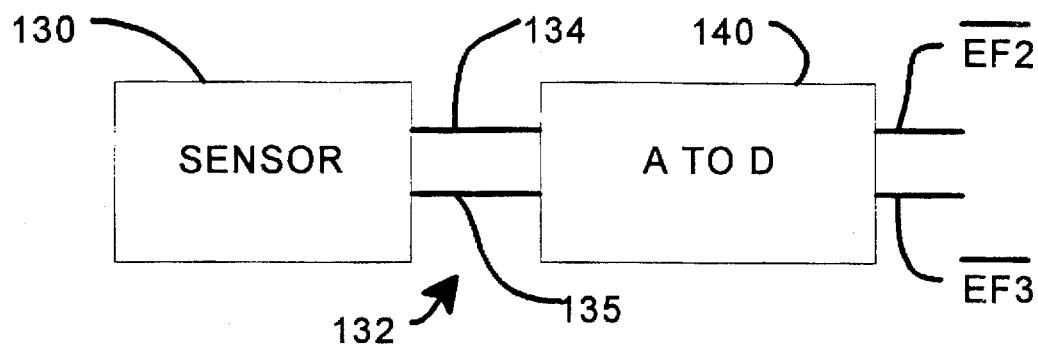
FIG. 2 is a schematic block diagram of a sensor and analog to digital converter circuit used in the preferred embodiment of the invention.

Referring to FIG. 2, the output of sensor 130 is coupled by a cable 132 comprising conductors 134 and 135 to the input of analog to digital converter 140. The output of the analog to digital converter is connected to terminals EF2 BAR and EF3 BAR shown in FIG. 11A of U.S. Pat. No. 4,692,147 ("'147 Patent"). Before converter 140 is connected to the terminals, the demodulator 101 currently shown in FIG. 11A would be disconnected.

The present invention may be implemented by providing seven different drug dosages from 0 dosage to a 1.0ml dosage with 0ml increments between choices. The time interval between dosages can be selected between one and twelve hours in seven choices. This is the same type of dosage and interval described in connection with device 10 shown in the '147 Patent (column 5, beginning at line 63). The seven drug dosages and corresponding time increments may be loaded into RAM 102a (FIG. 11B) of the '147 Patent. The appropriate drug dosage and interval is selected by a computer algorithm that reads the output of converter 140 and makes the appropriate selection.

Figure 3:
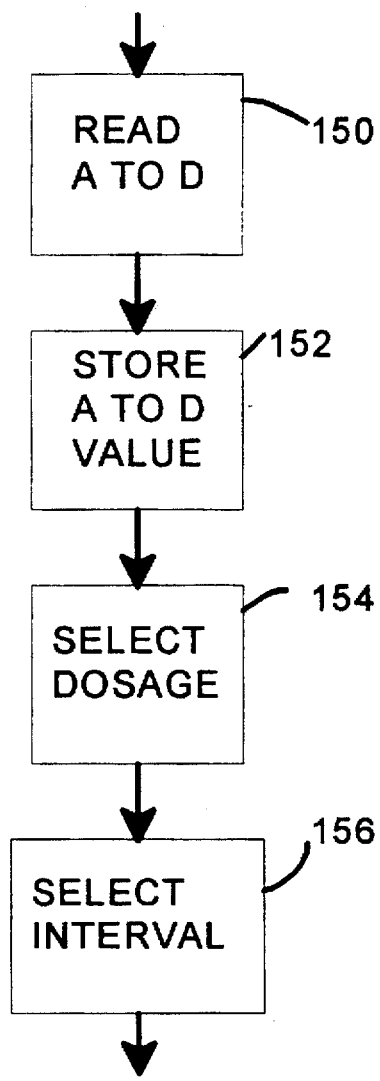
FIG. 3 is a flow chart illustrating a preferred form of a microprocessor program for utilizing the sensor to control the dosage of drug administered to the brain.

One exemplary computer algorithm is shown in FIG. 3. Microprocessor 100 included within device 10 reads converter 140 in step 150, and stores one or more values in RAM 102a in step 152. One of seven dosages is selected in step 154, and an appropriate time interval is selected in step 156. The selected dosage and interval of a drug is then delivered through catheter 22 and tube 22A to the basal ganglia of the brain by the pump of the type as described in the '147 Patent.

For some types of sensor, a microprocessor and analog to digital converter will not be necessary. The output from sensor 130 can be filtered by an appropriate electronic filter in order to provide a control signal for a pump of the type shown in the '147 Patent.

The type of drugs administered by device 10 into the brain depend on the specific location at which distal end 115 of tube 22A is surgically implanted. The appropriate drugs for use in connection with the portion of the basal ganglia or thalamus in which tube 22A terminates, together with the effect of the drug on that portion of the brain for reducing the hyperexcitation of the subthalamic nucleus for the purpose of treating Parkinson's degeneration is provided in Table I:

TABLE I

| EFFECT | PORTION OF BRAIN | DRUG |
|---|---|---|
| INCREASE EXCITATION | VL THALAMUS | glutamate agonist |
| DECREASE INHIBITION | VL THALAMUS | GABA antagonist |

TABLE I-continued

| EFFECT | PORTION OF BRAIN | DRUG |
|---|---|---|
| INCREASE INHIBITION | GPi/SNr | GABA agonist |
| DECREASE EXCITATION | GPi/SNr | Glutamate antagonist |
| INCREASE INHIBITION | STN | GABA agonist |
| DECREASE EXCITATION | STN | Glutamate antagonist |
| INCREASE EXCITATION | GPe | glutamate agonist |
| DECREASE INHIBITION | GPe | GABA antagonist |
| INCREASE DOPAMINE | NEOSTRIATUM | Dopamine agonist |

In the foregoing Table I, VL Thalamus means ventrolateral thalamus; GPi means internal segment of globus pallidus; SNr means substantia nigra pars reticulata, STN means subthalamic nucleus; and GPe means external segment of globus pallidus.

Alternative targets and infusion strategies are appropriate for treatement of degenerative disorders that are hyperkinetic in nature. For treatment of amyotrophic lateral sclerosis appropriate drugs for use in connection with the portion of the spinal cord, cerebral motor cortex, basal ganglia, and thalamus in which tube 22A terminates, together with the effect of the drug on that portion of the nervous system for decreasing excitation of the thalamic pathway is provided in Table II.

TABLE II

| EFFECT | TARGET STRUCTURE | DRUG |
|---|---|---|
| DECREASE EXCITATION | MOTOR CORTEX | GLUTAMATE ANTAGONIST |
| DECREASE EXCITATION | SPINAL CORD ANTERIOR HORN | PKC INHIBITOR |
| DECREASE EXCITATION | SPINAL CORD ANTERIOR HORN | GLUTAMATE ANTAGONIST |
| DECREASE EXCITATION | VL THALAMUS | GLUTAMATE ANTAGONIST |
| INCREASE INHIBITION | VL THALAMUS | GABA AGONIST |
| DECREASE INHIBITION | GPi/SNr | GABA ANTAGONIST |
| INCREASE EXCITATION | GPi/SNr | GLUTAMATE AGONIST |
| DECREASE INHIBITION | STN | GABA ANTAGONIST |
| INCREASE EXCITATION | STN | GLUTAMATE AGONIST |
| DECREASE EXCITATION | Gpe | GLUTAMATE ANTAGONIST |
| INCREASE INHIBITION | Gpe | GABA AGONIST |
| DECREASE DOPAMINE | NEOSTRIATUM | DOPAMIME ANTAGONIST |

Stereotaxic coordinates based on a normal brain for the portions of the brain described in Tables I and II are identified in the following Table III:

TABLE III

| BRAIN REGION | MEDIAL-LATERAL DIMENSION | DORSAL-VENTRAL DIMENSION | ANTERIOR-POSTERIOR DIMENSION |
|---|---|---|---|
| VL Thalamus | 0.7 to 1.8 | 1.5 to −0.2 | 0.0 to −1.0 |
| Gpi | 0.5 to 2.0 | 0.5 to −0.7 | 0.7 to 2.0 |
| SNr | 0.5 to 1.5 | −0.6 to −1.5 | 0.7 to −0.7 |
| STN | 0.5 to 2.0 | 0.0 to −1.0 | 0.6 to −1.0 |
| GPe | 1.6 to 2.7 | 1.0 to −1.0 | 2.0 to −1.0 |
| Striatum: | | | |
| Caudate | 0.5 to 2.0 | 1.5 to 3.0 | 1.5 to 3.0 |
| Putamen | 1.2 to 3.3 | 1.5 to −1.0 | 2.5 to −1.2 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to said line; all dimension are in centimeters.

Preferred ranges of dosages and specific drugs for the brain infusion sites identified in Tables I and II are provided in the following Table IV:

TABLE IV

| DRUG CLASS | SPECIFIC DRUG | DOSING RANGE |
|---|---|---|
| Glutamate Agonist | D-Cycloserine | 1–10 muM |
| | L-AP4 | 1–10 muM |
| | Carboxyphenylglycine | 10–500 muM |
| | L-glutamic acid | 1–100 muM |
| | cis-Piperidine-2,3-dicarboxylic acid | 1–10 muM |
| | (+/−)-trans-ACPD | 1–10 muM |
| | L-AP4 | 1–10 muM |
| Glutamate Antagonists | MK801(dizocilpine) | 1–20 muM |
| | ketamine Hcl | 5–50 muM |
| | AP-3 | 1–10 muM |
| | Dextromethorphan | 1–100 muM |
| | MCPD | 0.02–10 muM |
| | dextrorphan tartrate | 1–100 muM |
| | CNQX | 1–100 muM |
| GABA Agonists | baclofen | 0.1–10 muM |
| | muscinol HBr | 100–500 muM |
| GABA Antagonists | Gabazine | 1–50 muM |
| | Saclofen | 0.5–25 muM |
| | Bicuulline | 1–100 muM |
| | picrotoxin | 10–100 muM |
| Dopamine Antagonist | (+) apomorphine Hcl | 5–20 muM |
| | spiperone Hcl | 0.1–10 muM |
| | haloperidol | 10–100 muM |
| | (−) Sulpiride | 0.05–1 muM |
| Dopamine Agonist | methanesulfonate | 1–10 muM |
| | (−) apomorphine | 10–30 muM |
| | pergolide | |
| Anesthetic | Lidocaine hydrochloride | 5–20 muM |

In the preceding table, muM means micromolar.

Alternatively, these agents might be infused into the lateral ventricle or third ventricle of the brain or just beneath the dura above the cortex or in the intrathecal space. In this instance the drug would diffuse to the appropriate site of action.

Microprocessor 100 within device 10 can be programmed so that a controlled amount of drug can be delivered to the specific brain sites described in Tables I and II. Alternatively, sensor 130 can be used with a closed loop feedback system in order to automatically determine the level of drug delivery necessary to alleviate the hyperexcitation as described in connection with FIG. 3.

By using the foregoing techniques, neurodegenertive disorders can be controlled in a manner previously unattainable.

Those skilled in that art will recognize that the preferred embodiments may be altered or amended without departing from the true spirit and scope of the invention, as defined in the accompanying claims.

We claim:

1. A method of treating a neurodegenerative disorder by means of an implantable pump and a catheter having a discharge portion and having a proximal end coupled to said pump, said method comprising the steps of:

surgically implanting said catheter so that said discharge portion lies adjacent a predetermined infusion site in a brain; and operating said pump to discharge a predetermined dosage of at least one drug capable of altering the level of excitation of neurons of said brain through said discharge portion of said catheter into said infusion site, whereby neurodegeneration is prevented and said neurodegenerative disorder is therapeutically treated.

2. A method, as claimed in claim 1, wherein said step of implanting said catheter is performed as soon as practical after said neurodegenerative disorder is diagnosed.

3. A method, as claimed in claim 1, and further comprising the steps of:

implanting said pump outside said brain; and periodically refreshing the supply of said at least one drug to said pump outside said brain.

4. A method, as claimed in claim 1, wherein said neurodegenerative disorder is Parkinson's disease;

wherein said predetermined infusion site is selected from the group consisting of ventrolateral thalamus (Thal), internal segment of globus pallidus (GPi), substantia nigra pars reticulata (SNr), subthalamic nucleus (STN), external segment of globus pallidus (GPe), neostriatum, cerebral ventricle, subdural space, intrathecal space; and wherein said drug is selected to reduce hyperexcitation.

5. A method, as claimed in claim 4, wherein said at least one drug increases excitement of the thalamus.

6. A method, as claimed in claim 4, wherein said at least one drug increases inhibition of at least one of said internal segment of globus pallidus (GPi) and said substantia nigra pars reticulata (SNr) that inhibit thalamic output.

7. A method, as claimed in claim 4, wherein said at least one drug decreases excitement of the subthalamus.

8. A method, as claimed in claim 4, wherein said at least one drug decreases inhibition of said external segment of globus pallidus (Gpe).

9. A method, as claimed in claim 4, wherein said at least one drug is selected from the group consisting of a glutamate antagonist, a glutamate agonist, a γaminobutyric acid (GABA) antagonist, a γ-aminobutyric acid (GABA) agonist, a dopamine (DA) antagonist, a dopamine (DA) agonist and an anesthetic.

10. A method, as claimed in claim 4, wherein said at least one drug decreases inhibition of the thalamus.

11. A method, as claimed in claim 4, wherein said at least one drug decreases excitation of at least one of said internal segment of globus pallidus (GPi) and said substantia nigra pars reticulata (SNr) that inhibit thalamic output.

12. A method, as claimed in claim 4, wherein said at least one drug increases inhibition of the subthalamus.

13. A method, as claimed in claim 4, wherein said at least one drug increases excitation of said external segment of globus pallidus (Gpe).

14. A method, as claimed in claim 1, wherein said neurodegenerative disorder comprises amyotrophic lateral sclerosis, wherein said predetermined infusion site is selected from the group consisting of ventrolateral thalamus (Thal), internal segment of globus pallidus (GPi), substantia nigra pars reticulata (SNr), subthalamic nucleus (STN), external segment of globus pallidus (GPe), neostriatum, cerebral ventricle, subdural space, intrathecal space; and wherein said drugs is selected to reduce hyperexcitation.

15. A method, as claimed in claim 14, wherein said at least one drug decreases excitement of the thalamus.

16. A method, as claimed in claim 14, wherein said at least one drug decreases inhibition at least one of said internal segment of globus pallidus (GPi) and said substantia nigra pars reticulata (Snr).

17. A method, as claimed in claim 14, wherein said at least one drug decrease inhibition of said subthalamic nucleus (STN).

18. A method, as claimed in claim 14, wherein said at least one drug decreases excitation of at least one of said external segment of globus pallidus (GPe) and motorcortex and anterior horn of the spinal cord.

19. A method, as claimed in claim 14, wherein at least one drug decreases excitation of dopaminergic neurons in the neostriatum.

20. A method, as claimed in claim 4, wherein said at least one drug is selected from the group consisting of a glutamate antagonist, a glutamate agonist, a y-aminobutyric acid (GABA) antagonist, a y-aminobutyric acid (GABA) agonist, a dopamine (DA) antagonist, a dopamine (DA) agonist and an anesthetic.

21. A method, as claimed in claim 14, wherein said at least one drug increases inhibition of the thalamus.

22. A method, as claimed in claim 14, wherein said at least one drug increases excitation of at least one of said internal segment of globus pallidus (GPi) and said substantia nigra pars reticulata (Snr).

23. A method, as claimed in claim 14, wherein said at least one drug increases excitation of said subthalamic nucleus (STN).

24. A method, as claimed in claim 14, wherein said at least one drug increases inhibition of at least one of said external segment of globus pallidus (GPe), motorcortex and anterior horn of the spinal cord.

25. A method, as claimed in claim 1, wherein said neurodegenerative disorder comprises Huntington's disease;

wherein said predetermined infusion site is selected from the group consisting of ventrolateral thalamus (Thai), internal segment of globus pallidus (GPi), substantia nigra pars reticulata (SNr), subthalamic nucleus (STN), external segment of globus pallidus (GPe), neostriatum, cerebral ventricle, subdural space, intrathecal space; and wherein said drug is selected to reduce hyperexcitation.

* * * * *

UNITED STATES PATENT AND TRADEMARK OFFICE
CERTIFICATE OF CORRECTION

PATENT NO.: 5,735,814

DATED: April 7, 1998

INVENTOR(S): Elsberry et al.

It is certified that error appears in the above-identified patent and that said Letters Patent is hereby corrected as shown below:

Column 7, Line 54 reads "γaminobutyric" and should read -- γ-aminobutyric --

Column 7, Line 54 reads "agonist, a a" and should read -- agonist, a --.

Column 8, Line 55 reads "(Thai)" and should read -- (Thal) --

Signed and Sealed this

Fifteenth Day of February, 2000

Q. TODD DICKINSON

*Attest:*

*Attesting Officer*  *Commissioner of Patents and Trademarks*